United States Patent
Strouse et al.

(10) Patent No.: US 10,571,782 B2
(45) Date of Patent: Feb. 25, 2020

(54) PORTABLE IMAGE DIAGNOSTIC APPARATUS AND SYSTEM

(71) Applicant: Research Institute at Nationwide Children's Hospital, Columbus, OH (US)

(72) Inventors: Robert V. Strouse, Columbus, OH (US); Jeremy Patterson, Columbus, OH (US); Kara Rood, Canal Winchester, OH (US); Irina Buhimschi, Columbus, OH (US)

(73) Assignee: Research Institute at Nationwide Children's Hospital, Columbus, OH (US)

(*) Notice: Subject to any disclaimer, the term of this patent is extended or adjusted under 35 U.S.C. 154(b) by 0 days.

(21) Appl. No.: 15/777,100

(22) PCT Filed: Nov. 15, 2016

(86) PCT No.: PCT/US2016/062025
§ 371 (c)(1),
(2) Date: May 17, 2018

(87) PCT Pub. No.: WO2017/087381
PCT Pub. Date: May 26, 2017

(65) Prior Publication Data
US 2018/0373125 A1 Dec. 27, 2018

Related U.S. Application Data

(60) Provisional application No. 62/256,456, filed on Nov. 17, 2015.

(51) Int. Cl.
*G03B 17/56* (2006.01)
*G06K 9/32* (2006.01)
*G06T 7/00* (2017.01)

(52) U.S. Cl.
CPC ........ *G03B 17/561* (2013.01); *G03B 17/565* (2013.01); *G06K 9/3233* (2013.01); *G06T 7/0002* (2013.01)

(58) Field of Classification Search
USPC ........................................................ 396/419
See application file for complete search history.

(56) References Cited

U.S. PATENT DOCUMENTS

| 5,764,409 A | 6/1998 | Colvin |
| 2013/0057927 A1 | 3/2013 | Durant et al. |

(Continued)

OTHER PUBLICATIONS

PCT International Search Report (ISR) from corresponding application No. PCT/US2016/062025 filed Nov. 15, 2016 claiming priority to U.S. Appl. No. 62/256456, ISR dated Jan. 23, 2017, (2 pages).

(Continued)

*Primary Examiner* — Clayton E. LaBalle
*Assistant Examiner* — Warren K Fenwick
(74) *Attorney, Agent, or Firm* — John A. Yirga, Esq.; Tarolli, Sundheim, Covell & Tummino LLP

(57) ABSTRACT

An apparatus and system for analyzing one or more points of interest. The apparatus includes a main support having first and second legs. The first and second legs extending transversely from the main support. The main support nests an imaging device capable of capturing an image of a point of interest during use. An imaging shroud is coupled to and extending from the first leg, the shroud having a first opening for surrounding the point of interest. A second opening in the shroud is positioned such that it extends to be within the main support for the passage of a captured image of the point of interest during use.

20 Claims, 8 Drawing Sheets

(56) References Cited

U.S. PATENT DOCUMENTS

| | | |
|---|---|---|
| 2013/0267283 A1 | 10/2013 | Guzman |
| 2014/0072362 A1 | 3/2014 | Hyers |
| 2014/0375803 A1* | 12/2014 | Quilter ............. G01N 35/00871 348/143 |
| 2015/0042873 A1* | 2/2015 | Hunt ................... H04N 5/2254 348/373 |
| 2015/0172522 A1* | 6/2015 | O'Neill ............... H04N 5/2252 348/240.3 |
| 2015/0253255 A1* | 9/2015 | Wagner ................. G01N 21/87 356/30 |

OTHER PUBLICATIONS

PCT International Preliminary Report on Patentability (IPR) from corresponding application No. PCT/US2016/062025 filed Nov. 15, 2016 claiming priority to U.S. Appl. No. 62/256,456, IPR dated Jan. 23, 2017. (8 pages).

* cited by examiner

PORTABLE IMAGE DIAGNOSTIC APPARATUS AND SYSTEM

CROSS REFERENCES TO RELATED APPLICATIONS

The following application claims priority under 35 U.S.C. § 371 to co-pending International Patent Application Serial No. PCT/US2016/062025 that was filed on Nov. 15, 2016 and published on May 26, 2017 under international publication number WO 2017/087,381, which claims priority under 35 U.S.C. § 119(e) to U.S. Provisional Patent Application Ser. No. 62/256,456 filed Nov. 17, 2015 entitled PORTABLE IMAGE DIAGNOSTIC APPARATUS AND SYSTEM. The above-identified applications and publication are incorporated herein by reference in their entireties for all purposes.

TECHNICAL FIELD

The present disclosure relates generally to a portable image diagnostic apparatus, and more specifically, a portable image diagnostic system for analyzing overtime one or more points of interest while controlling one or more external variables.

BACKGROUND

A point of interest are associated with living beings or non-living objects that change shape, contour, or size over a period of time, ranging from a few seconds to years. For example, a point of interest may include, but is not limited to, skin imperfections such as a mole or cancerous cells, stress fractures in a bridge or building structure, or changes in biological samples. It should be appreciated by those or ordinary skill in the art, why the tracking of such points of interest are of concern for safety and/or are of educational value.

Advancements in imaging devices or image capturing technologies, such as cameras and phones supporting the cameras now make high resolution imaging more available to users tracking points of interest in their respective professions. However, there is no known device or method that controls the external variables encountered when using these advanced imaging devices. As a result, variability occurs in the data collection, skewing that data analysis.

SUMMARY

One aspect of the present disclosure includes an apparatus and system for analyzing one or more points of interest. The apparatus includes a main support having at least a first leg. The first leg extends transversely from said main support. The main support is for nesting an imaging device capable of capturing an image of a point of interest during use. The apparatus further includes an imaging shroud coupled to and extending from said first leg. The shroud has a first opening and a second opening. The first opening is for surrounding the point of interest and said second opening is positioned to extend into said main support for capturing the image of the point of interest during use.

One aspect of the present disclosure includes a method for analyzing one or more points of interest. The method comprising the steps of providing an apparatus for analyzing one or more points of interest, providing a main support on the apparatus, the main support having at least a first leg and extending transversely the first leg from the main support. The method further comprises forming a nesting area within the main support for an imaging device capable of capturing an image of a point of interest during use; providing an imaging shroud coupled to and extending from the first leg; and spacing a first opening from a second opening in the shroud. The first opening for surrounding the point of interest during use and the second opening positioned to extend into the main support for capturing an image of the point of interest during use.

One aspect of the present disclosure includes a system for analyzing one or more points of interest. The system comprising an apparatus for performing at least one of capturing and analyzing one or more points of interest. The apparatus comprising a main support having first and second legs. The first and second legs extend transversely from said main support. The main support is for nesting an imaging device capable of capturing an image of a point of interest during use. The apparatus further comprises an imaging shroud coupled to and extending from said first leg. The shroud has a first opening a fixed distance from a second opening. The first opening is for surrounding the point of interest and is formed along a single plane. The second opening is positioned to extend into the main support for capturing the image of the point of interest during use. The system further comprises an imaging device. The imaging device is positioned within the main support to align an image capturing portion of the imaging device with the second opening within the main support during use.

BRIEF DESCRIPTION OF THE DRAWINGS

The foregoing and other features and advantages of the present disclosure will become apparent to one skilled in the art to which the present disclosure relates upon consideration of the following description of the invention with reference to the accompanying drawings, wherein like reference numerals, unless otherwise described refer to like parts throughout the drawings and in which.

Figure 1A:
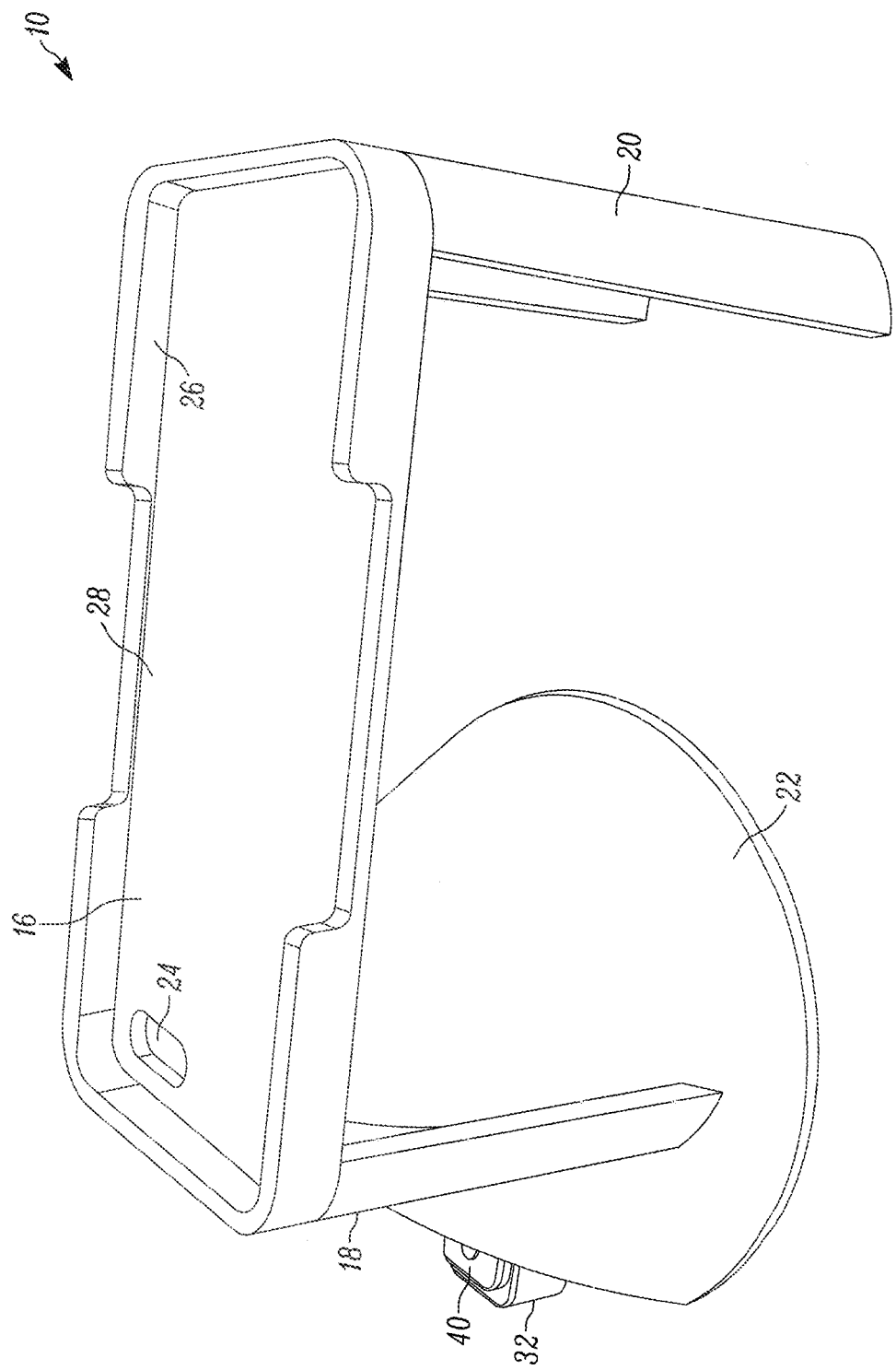
FIG. 1A is a portable image diagnostic apparatus constructed in accordance with one example embodiment of the present disclosure.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

Referring now to the figures wherein like numbered features shown therein refer to like elements throughout unless otherwise noted. The present disclosure relates generally to a portable image diagnostic apparatus, and more specifically, a portable image diagnostic system for analyzing overtime one or more points of interest while controlling one or more external variables.

Illustrated in FIG. 1A is a portable image diagnostic apparatus 10 constructed in accordance with one example embodiment of the present disclosure. The apparatus 10 allows for an analyzing of one or more points of interest 12 (see FIG. 4) using an imaging device 14 (see FIG. 2A). The points of interest 12 are associated with living beings or non-living objects that change shape, contour, or size over a period of time, ranging from a few seconds to years. For example, a point of interest 12 may include, but is not limited to, skin imperfections such as a mole or cancerous cells, stress fractures in a bridge or building structure, or changes in biological samples.

Figure 1B:
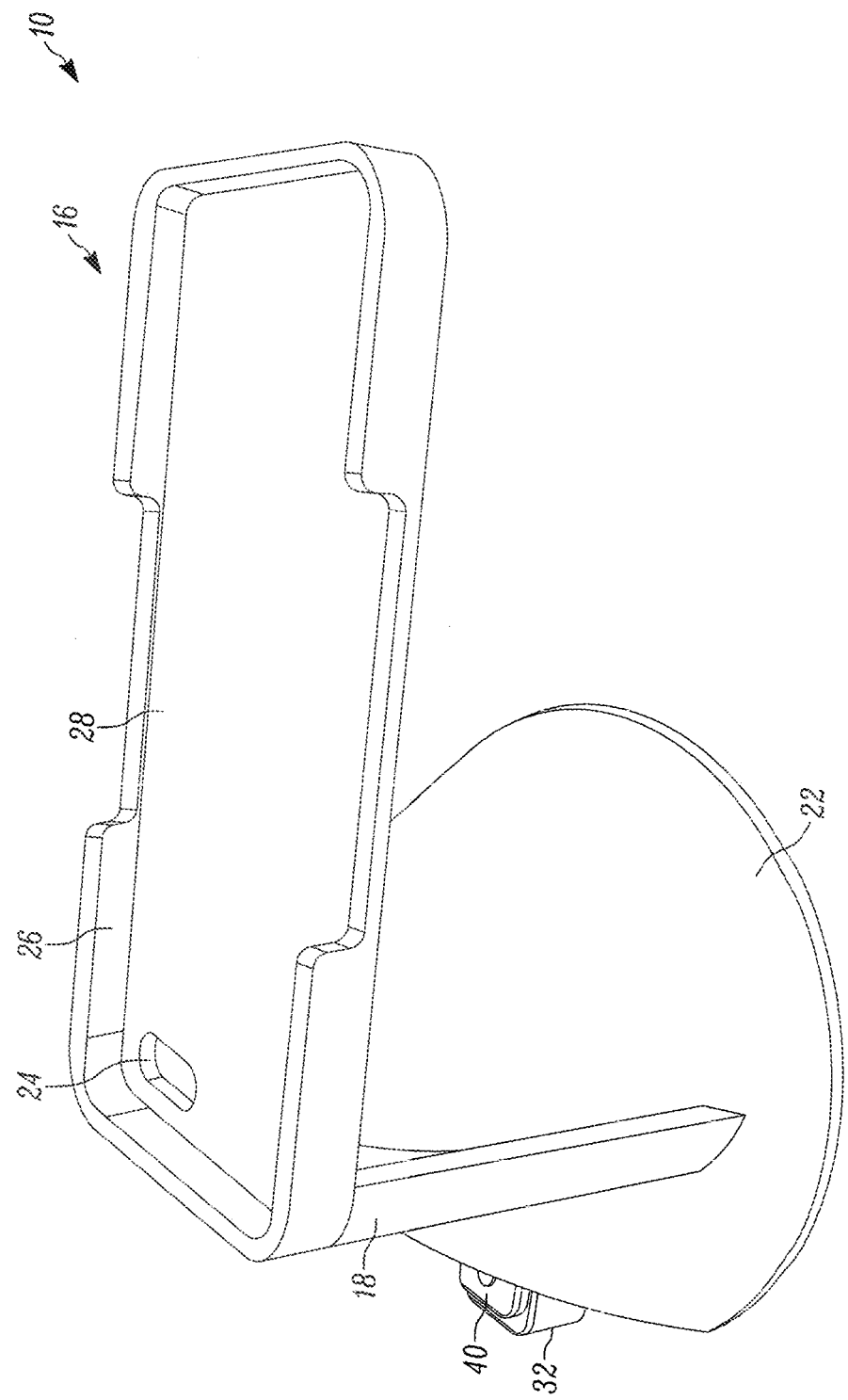
FIG. 1B is a portable image diagnostic apparatus constructed in accordance with a second example embodiment of the present disclosure.

In the illustrated example embodiment, the diagnostic apparatus 10 is constructed of various molded plastic pieces that snap together to form the apparatus. It should be appreciated that other materials of similar strength and weight could be used without departing from the spirit and scope of the present disclosure. In one example embodiment, the apparatus 10 includes a main support 16 elevated by first and second spaced legs 18, 20, respectively. The first leg 18 is molded into an imaging shroud 22. In one example embodiment, the imaging shroud 22 is at least one of conical, square, cone shaped, or the like. In another example embodiment, the apparatus 10 includes the main support 16 elevated by the first leg 18 molded into the imaging shroud 22, wherein the second leg 20 is detached/not present (see FIG. 1B). The main support 16 includes a circumferential lip 26 surrounding a base 28 to nest the imaging device 14. In one example embodiment, the circumferential lip 26 is configured to fit the imaging device 14, such that the imaging device is maintained in a constant position within the main support 16. In another example embodiment, the imaging device 16 snaps into the main support via interaction with the lip 16. The support 16 further includes an imaging aperture 24 for the passing of one or more images or photographs 50 captured by the imaging device 14.

Figure 2A:
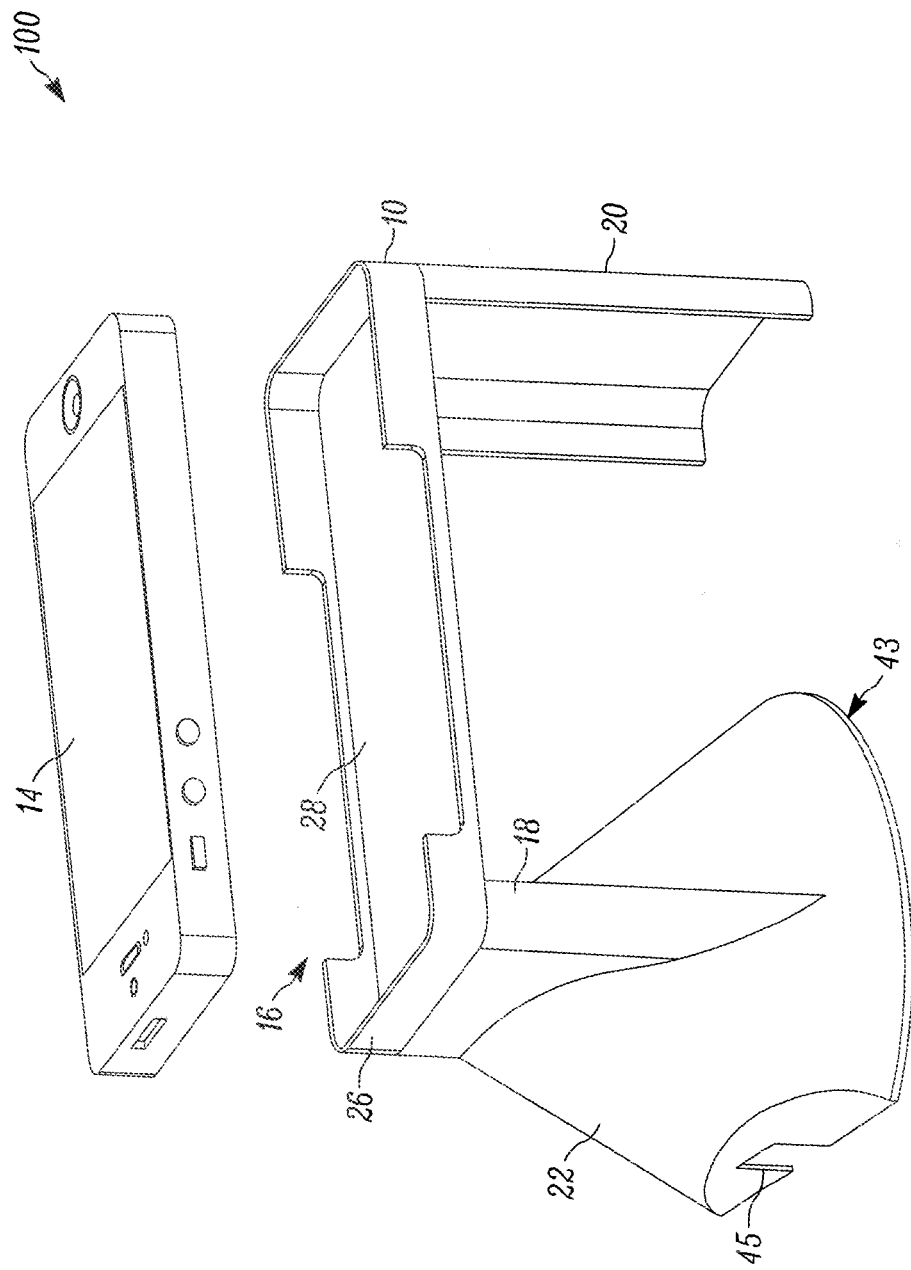
FIG. 2A is an exploded assembly view of a portable image diagnostic system constructed in accordance with one example embodiment of the present disclosure.
Figure 2B:
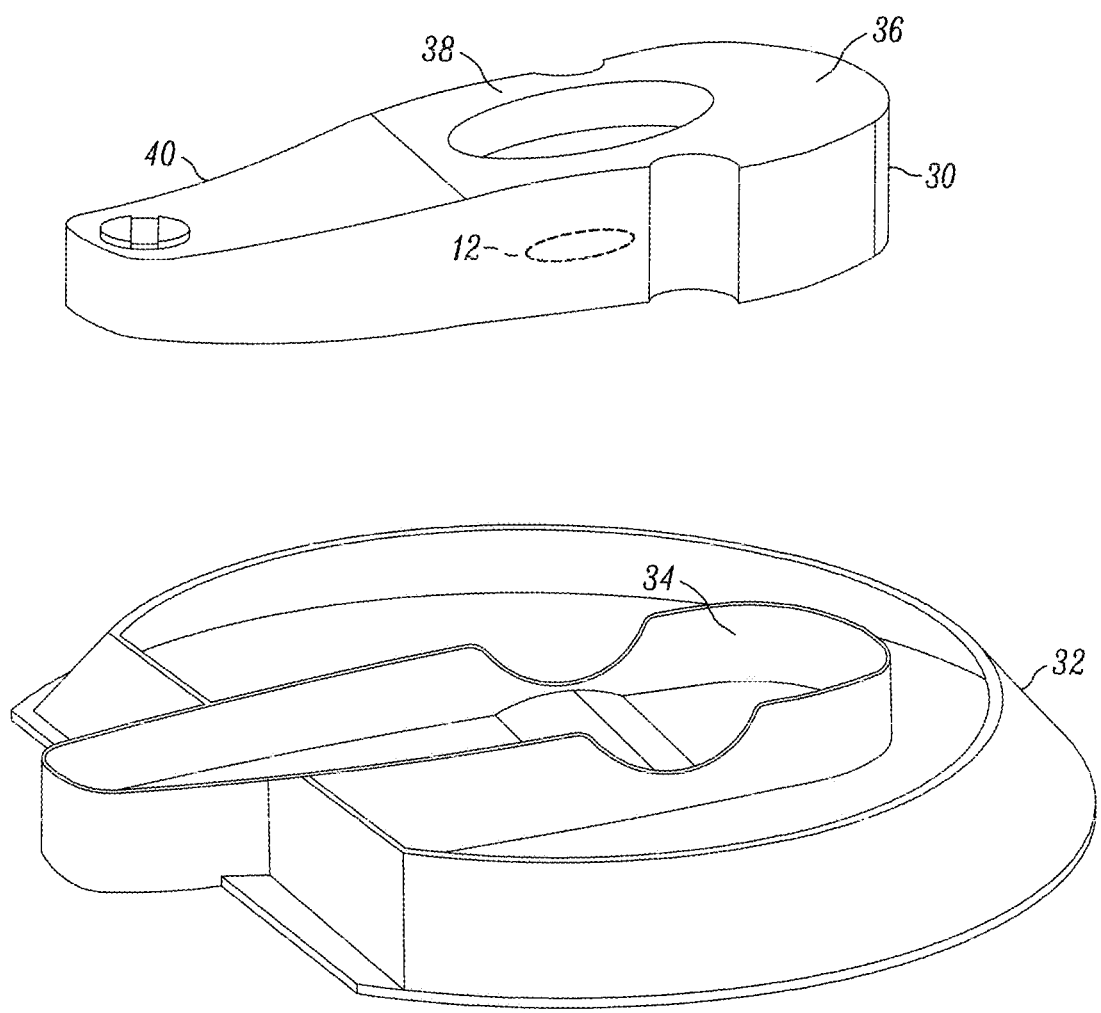
FIG. 2B is an exploded assembly view of a fixture assembly of a portable image diagnostic system constructed in accordance with one example embodiment of the present disclosure.
Figure 3:
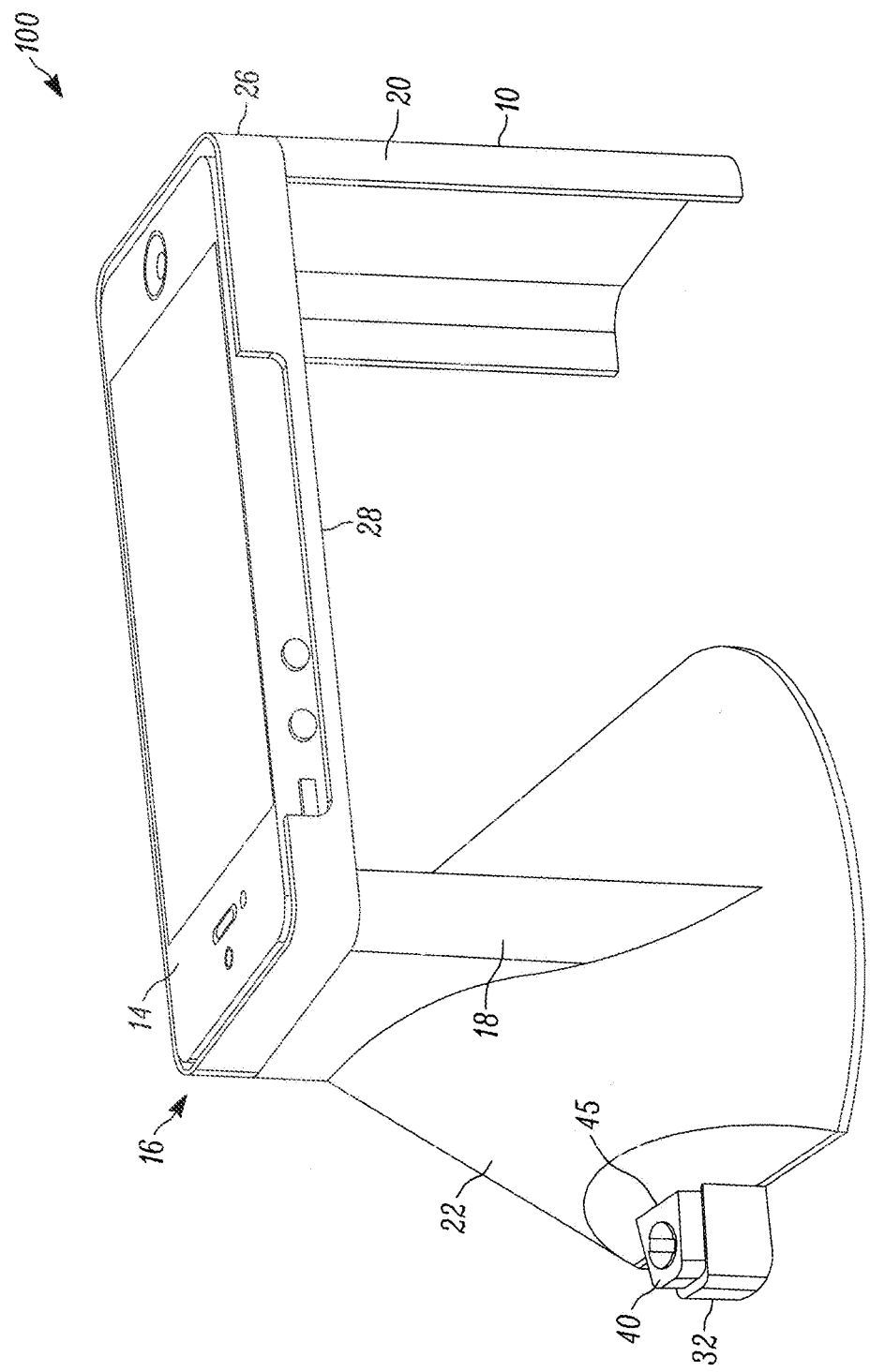
FIG. 3 is an assembled view of FIGS. 2A and 2B.

FIGS. 2A-2B are exploded assembly views of a portable image diagnostic system 100 constructed in accordance with one example embodiment of the present disclosure. The system 100 includes a fixture 30, a fixture support 32 (see FIG. 2B), the imaging device 14, and the diagnostic apparatus 10 that are assembled in FIG. 3. It should be appreciated that though the imaging device 14 is illustrated having a rectangular shape, the diagnostic apparatus 10 can be configured to nest various imaging devices having various shapes.

The fixture 30 is molded such that the fixture support 32 includes a housing 34 for nesting the fixture when images are captured by the imaging device 14. The fixture 30 provides a reference point 36 of a known size to compare to the size of the point of interest 12 over time, assisting to indicate if any a change in size, shape, or contour of the point of interest has changed. The fixture 30 includes a recess 38 and a handle 40. The handle 40 facilitates the positioning of the fixture 30 within the housing 34 of the support 32. In one example embodiment, the recess 38 provides a holding seat for an object comprising the point of interest 12 if it is removable, such as a piece of tissue. The fixture 30 may further comprise an identification number or tag that aids in tracking the captured image 50. In another example embodiment, the recess 38 provides the holding seat for a test strip, cassette, or the like, wherein the test strip remains stationary. For example, responsive to the test strip comprising a color indicator, the color indicator will comprise the point of interest 12. In this example, the color change is easily viewed as a function of time, as the distance, light, etc. are controlled by the system 100.

The imaging shroud 22 includes a first opening or an aperture 24 (see FIGS. 1A, 1B, and 4) for the passing and capturing an image 50 by the imaging device 14 and a second opening 43 for surrounding a point of interest 12. In one example embodiment, the second opening 43 is formed in a single plane, thus forming a seal to prevent the entry of external light into the shroud 22. In another example embodiment, the seal is formed by a shroud base 54 that defines the second opening 43. In another example embodiment, the shroud 22 includes an opening 45 for permitting entry of the fixture 40.

Figure 4:
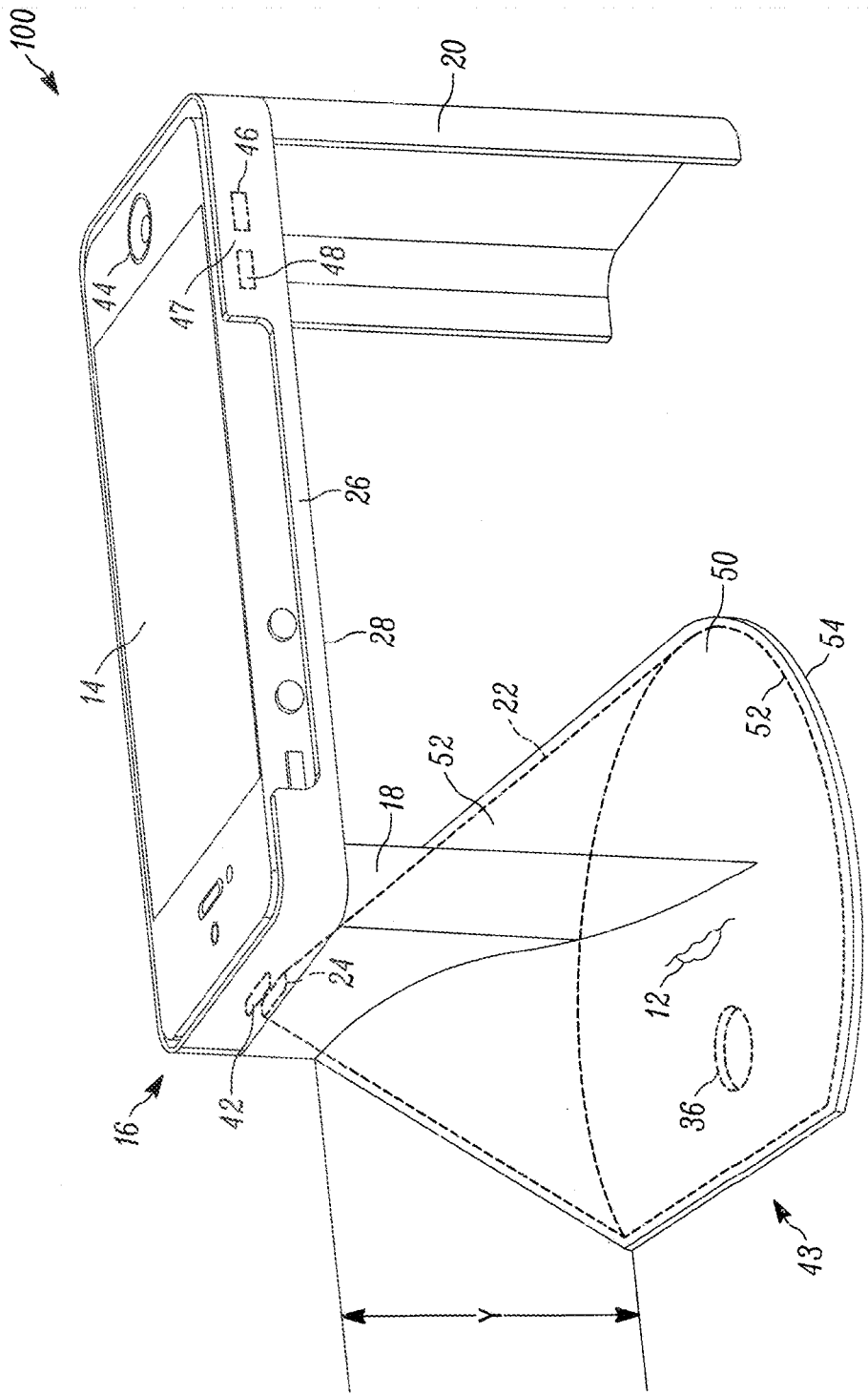
FIG. 4 is portable image diagnostic system capturing a point of interest in accordance with one example embodiment of the present disclosure.

In the illustrated example embodiment of FIG. 4 that includes the system 100 capturing the point of interest 12, the imaging device 14 is a small computer or phone having a camera 42 for capturing an image. One suitable example of an imaging device is an Apple® iPhone or iPod operating on a Apple operating system of 4s or higher and having a camera with at least 4 mega pixels ("4 MP"). The imaging device 14 in the illustrated example embodiment of FIG. 4 further comprises an actuation button 44 for initiating the camera 42 and an internal processor 46 coupled to internal memory 48 for processing and storing one or more images 50.

In one embodiment, when the actuating button 44 is engaged, an image 50 is captured by the camera 42 and stored in the imaging device's memory 48 via the processor 46. When the image 50 is captured, a focal pattern or window 52 is projected by the camera 42. The focal pattern or window 52 is calculated such that it lies just inside the perimeter of the imaging shroud 22. Because a distance ("y") from the shroud base 54 to the imaging sensor capturing the image 50 by the camera lens is constant and the shroud 22 encloses or surrounds (eliminating variations in light) the point of interest 12, the recapturing of the point of interest at a later time is repeatable. Thus, the apparatus 10 and its construction as shown in FIGS. 1-4, control all external variables and allow for standardized, uniform, and a repeatable collection of data about one or more points of interest 12 in a non-destructive testing fashion.

While the shroud 22 resembles a cone with a substantially circular base 54, other geometrical shapes, such as squares and polygons are contemplated and a person having ordinary skill in the art would understand various shroud geometries to be within the spirit and scope of the present disclosure.

Figure 5:
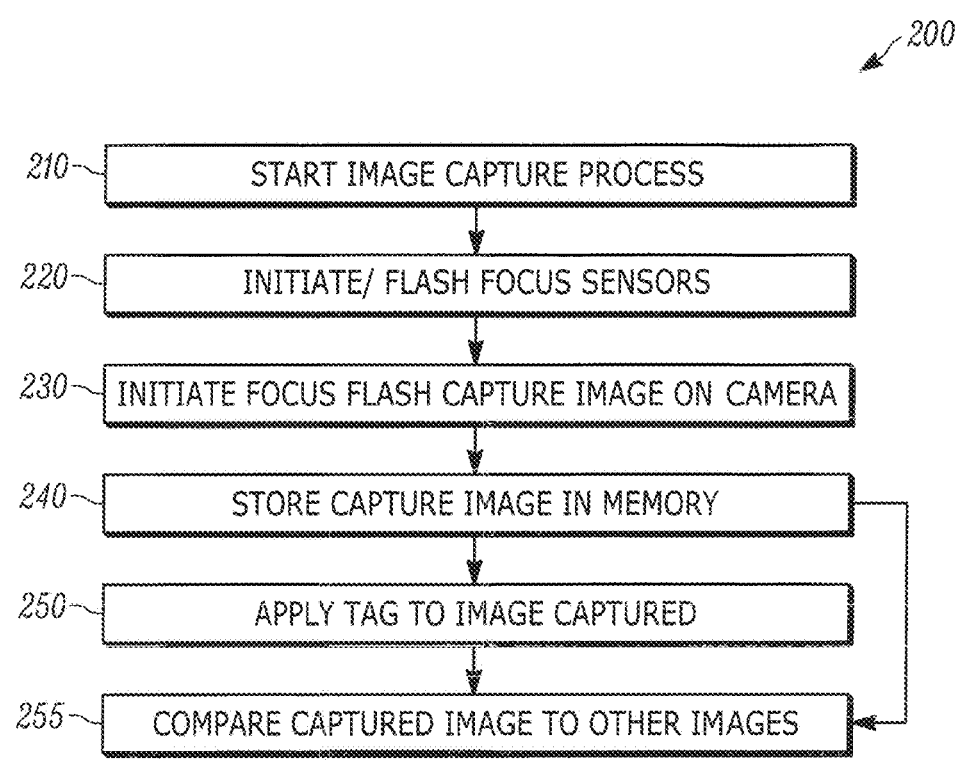
FIG. 5 is a process flow diagram of a portable image diagnostic system in accordance with one example embodiment of the present disclosure.

FIG. 5 is a process flow diagram of a portable image diagnostic system process 200 in accordance with one example embodiment of the present disclosure. The process 200 is executed by the processor 46 and images are captured by instructions from a computer readable medium 47. Wherein, the computer readable medium 47 as used herein refers to a medium or media that participates in providing instructions to the processor or computer 46 for execution. In another example embodiment, the computer readable medium 47 is software and/or firmware running on designated and/or remote platforms having separate processing capabilities. Alternatively, the computer readable medium 47 is hardware such as an application specific integrated circuit ("ASIC"), or is a combination software running on a processor and ASIC.

In yet another example embodiment, the computer readable medium 47 is internal or external to the processor 46, or a network of computers and computing devices, local and wide area networks, remote storage clouds, and remote server web-linked computers, such as the Internet, all collectively acting as a computer system. It will thus be appreciated that the computer readable medium 47 is non-transitory and can include multiple discrete media that are operatively connected to the processing unit 46, for example, via one or more of a local bus, input/output connections, hardware connections, or a network connection.

The process 200 starts at step 210, as illustrated in FIG. 5. At 220, the process 200 includes the initiating of flash and focus sensors of the camera 42. At 230, the process continues as the focus, flash, and image capture hardware are initiated by the processor 46 by executable instructions found in the non-transitory readable medium 47. At 240, the process advances by storing a captured image 50 in the memory 48. At 250, the process 200 continues by applying a tag to the captured image 50 (e.g., a time tag, an ID tag, etc). At 255, the process 200 continues by comparing the captured image 50 to other previous or subsequently captured images obtained by the system 100. Alternatively, the process 240 continues to the step at 255 to compare images to other images without applying a tag to the captured image 50.

In executing the process 200, a reference point 36 is included in the captured image 50 (see FIG. 4). The reference point 36 provides a legend or fixed scale for measuring changes in the point of interest 12. Examples of such reference points 36 include, but are not limited to, QR code, geo tag, known coin, such as a quarter, and the like.

Figure 6:
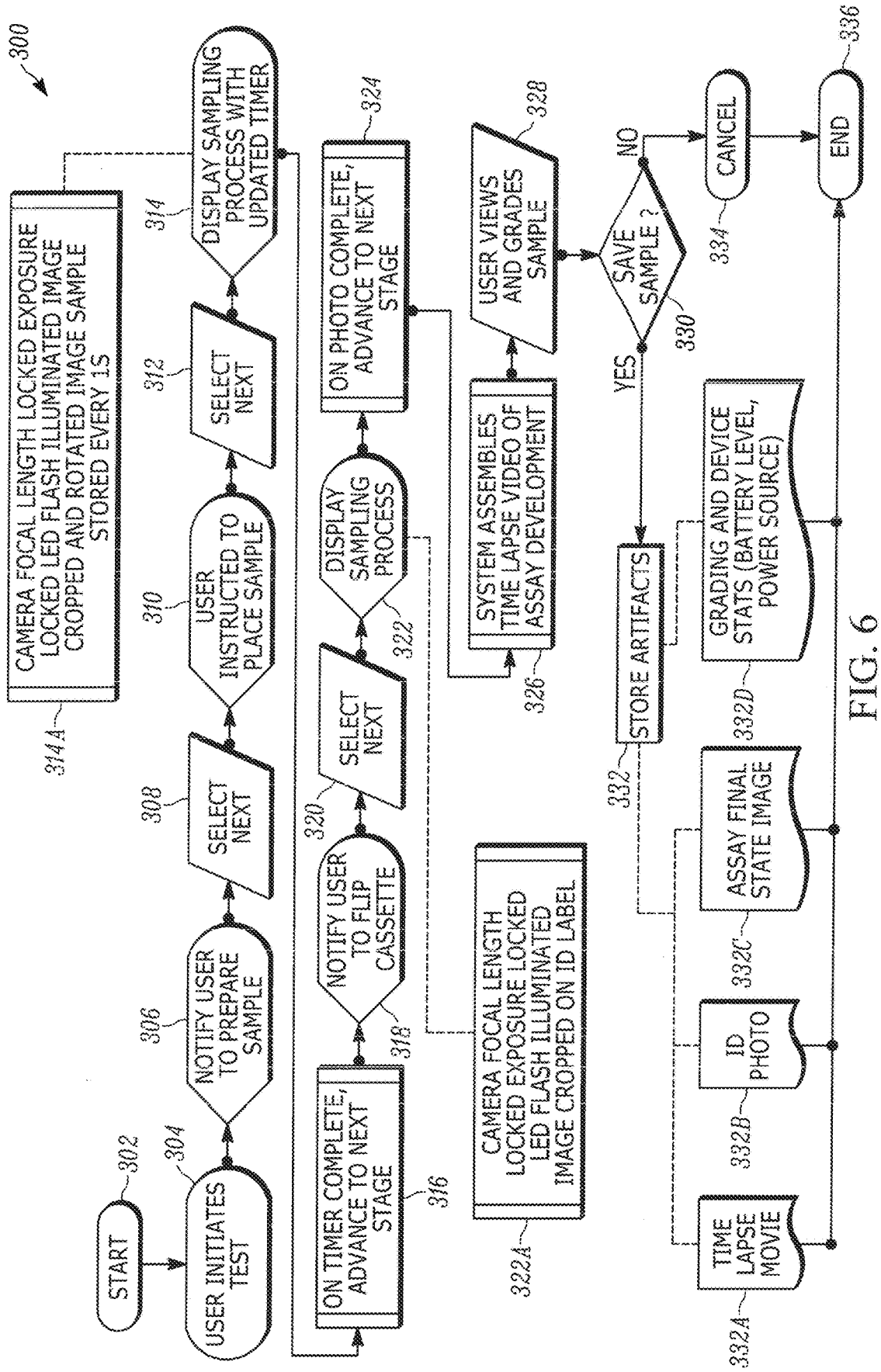
FIG. 6 is a process flow diagram of a portable image diagnostic system in accordance with another example embodiment of the present disclosure.

Illustrated in FIG. 6 is a process flow diagram 300 of a portable image diagnostic system 100 operating in accordance with another example embodiment of the present disclosure. At 302 the process 300 starts. At 304, a user initiates a test, such as a test strip or cassette, wherein a color or other visual indicator changes over time. At 306, the user is notified to prepare a sample, such as by software/hardware present on the imaging device 14. At 308, responsive to the user preparing the sample, the user selects next. At 310, the user is instructed to place the sample under the shroud 22 or on a designated area on the fixture 30. In one example embodiment, the user is instructed by the imaging device 14. At 312, responsive to the user placing the sample under the shroud 22, the user selects next. At 314, the imaging device 14, or an associated device with display capabilities, displays a sampling process with an updated timer. In one example embodiment, such as at 314A, the sampling process comprises locking a focal length, an exposure time, and/or a flash illumination intensity of the camera 42, as well as a duration between image captures (e.g., one image may be taken and stored every second, or some other duration). In another example embodiment, the sampling process designates an area of interest under the shroud 22 and crops non-interesting areas and/or rotates the area of interest for viewing ease of the user.

At 316, responsive to the timer being complete, the user advances to a next stage, if applicable (e.g., such as when the strip or cassette is double sided). At 318, the user is notified to flip the strip or cassette. At 320, responsive to the user flipping the strip or cassette, the user selects next. At 322, the imaging device 14, or an associated device with display capabilities, displays a sampling process in a same or similar manner as at 314, wherein the sampling process 322a is the same or similar to the sampling process 314a. At 324, upon photo completion, the system 100 advances to a next stage, where, as depicted at 326, the system assembles a time lapse video of, for example, an assay present on the strip or cassette as it develops. In one example embodiment, a single strip may comprise many assays, which have various time points for assay readings, making the time lapse video valuable and efficient for taking and interpreting readings. At 328, the user views and grades the sample based upon a clarity of the assay readings on the strip or cassette. At 330, the user may save the sample if the sample is adequate, or erase the sample if the sample is not adequate. If the user chooses not to save the sample, then the user will select cancel as depicted at 334, and the process 300 will end. If the user chooses to save the sample, then the user will opt to store artifacts, as depicted at 332, and the process 300 will end, as depicted at 336. In one example embodiment, the artifacts stored at 332 comprise at least one of a time lapse movie 332A, an ID photo 332B (e.g., the reference point 36), an assay final state image 332C (e.g., an image of the assay at the end of the timer), and/or grading and device stats (e.g., how the user graded the sample, a battery level of the imaging device 14, etc.).

It should be appreciated that the imaging device 14 may implement the process 200 or 300 in a similar fashion, but instead of capturing several images 50 the device could use the apparatus 10 to capture video of the point of interest 12 over an extended period of time. Additionally, it should be appreciated that once the images 50 are captured, the imaging device 14 can be inverted or flipped so that the captured image can be displayed to the user on a screen located on one of the sides of the imaging device. Such a large display allows for grading and tagging of the images 50 and comparing image results against other images captured at different points of time.

In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art. In one non-limiting embodiment the terms are defined to be within for example 10%, in another possible embodiment within 5%, in another possible embodiment within 1%, and in another possible embodiment within 0.5%. The term "coupled" as used herein is defined as connected or in contact either temporarily or permanently, although not necessarily directly and not necessarily mechanically. A device or structure that is "configured" in a certain way is configured in at least that way, but may also be configured in ways that are not listed.

To the extent that the materials for any of the foregoing embodiments or components thereof are not specified, it is to be appreciated that suitable materials would be known by one of ordinary skill in the art for the intended purposes.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. An apparatus for analyzing one or more points of interest, the apparatus comprising:
    a main support having at least a first leg, said first leg extending transversely from said main support, the main support for nesting an imaging device capable of capturing an image of a point of interest during use;
    an imaging shroud coupled to and extending from said first leg, the shroud having a first opening and a second opening, the first opening for surrounding the point of interest and said second opening positioned to extend into said main support for capturing the image of the point of interest during use; and
    a fixture configured to be nested within the shroud.

2. The apparatus of claim 1 further comprising a system that includes the imaging device, the imaging device being positioned within the main support during use.

3. The apparatus of claim 2 wherein the imaging device is positioned to align with the second opening within the main support during use.

4. The apparatus of claim 1, wherein said first opening is formed in a single plane.

5. The apparatus of claim 4, wherein said single plane is at least one of transverse or parallel to a plane one which the support extends.

6. The apparatus of claim 1 wherein said shroud maintains a fixed distance between said first and second openings.

7. The apparatus of claim 1 wherein said first opening comprises a fixture notch configured to nest the fixture.

8. The apparatus of claim 7 wherein said fixture comprises a stationary reference point used to reference the point of interest during use.

9. The apparatus of claim 1 wherein the main support comprises a base and a lip, the lip circumferentially encircling the base, and wherein the second opening extends through the base.

10. The apparatus of claim 9 wherein the lip positions an image capturing portion of the imaging device to align with the second opening within the main support during use.

11. The apparatus of claim 1 comprising a second leg spaced from the first leg and coupled to the main support.

12. A method for analyzing one or more points of interest, the method comprising the steps of:
    providing an apparatus for analyzing one or more points of interest;
    providing a main support on the apparatus, the main support having at least a first leg and extending transversely from said support;
    forming a nesting area within the main support for an imaging device capable of capturing an image of a point of interest during use;
    providing an imaging shroud coupled to and extending from said first leg; and
    spacing a first opening from a second opening in the shroud, the first opening comprising a notch configured to nest a fixture, the first opening for surrounding the point of interest during use and said second opening positioned to extend into said main support for capturing an image of the point of interest during use.

13. A system for analyzing one or more points of interest, the system comprising:
    an apparatus for analyzing one or more points of interest, the apparatus comprising:
        a main support having first and second legs, said first and second legs extending transversely from said main support, the main support for nesting an imaging device capable of capturing an image of a point of interest during use; and
        an imaging shroud coupled to and extending from said first leg, the shroud having a first opening a fixed distance from a second opening, the first opening is for surrounding the point of interest and is formed along a single plane and said second opening is positioned to extend into said main support for capturing the image of the point of interest during use, the imaging shroud is couplable to a defined stationary reference point used to reference the point of interest during use; and
    an imaging device, the imaging device being positioned within the main support to align an image capturing portion of the imaging device with the second opening within the main support during use.

14. The system of claim 13, wherein said single plane is at least one of transverse or parallel to a plane one which the main support extends.

15. The system of claim 13 wherein said first opening comprises a fixture notch configured to nest an assembled fixture.

16. The system of claim 15 wherein said assembled fixture comprises the stationary reference point used to reference the point of interest during use.

17. The system of claim 15 wherein said assembled fixture comprises a fixture and a fixture support that nests the fixture and maintains a constant position of the fixture relative to the shroud.

18. The system of claim 13 wherein the main support comprises a base and a lip, the lip circumferentially encircling the base, and wherein the second opening extends through the base.

19. The system of claim 18 wherein the lip positions the imaging device to align an image capturing portion of the imaging device with the second opening within the main support during use.

20. The system of claim 13 wherein the first opening is larger than the second opening.

\* \* \* \* \*